(12) United States Patent
Lippert

(10) Patent No.: US 11,883,639 B2
(45) Date of Patent: Jan. 30, 2024

(54) GEAR PUMP

(71) Applicant: Fresenius Medical Care Deutschland GmbH, Bad Homburg (DE)

(72) Inventor: Simone Lippert, Gemuenden am Main (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 222 days.

(21) Appl. No.: 17/425,972

(22) PCT Filed: Jan. 27, 2020

(86) PCT No.: PCT/EP2020/051944
§ 371 (c)(1),
(2) Date: Jul. 27, 2021

(87) PCT Pub. No.: WO2020/157015
PCT Pub. Date: Aug. 6, 2020

(65) Prior Publication Data
US 2022/0047861 A1  Feb. 17, 2022

(30) Foreign Application Priority Data
Jan. 28, 2019 (DE) .................... 10 2019 102 073.5

(51) Int. Cl.
*F04C 2/08* (2006.01)
*F04C 15/00* (2006.01)
(Continued)

(52) U.S. Cl.
CPC ........ *A61M 60/113* (2021.01); *A61M 60/253* (2021.01); *A61M 60/37* (2021.01); *A61M 60/457* (2021.01); *A61M 60/845* (2021.01); *F04C 2/08* (2013.01); *F04C 14/26* (2013.01); *F04C 15/06* (2013.01); *F04C 2210/1016* (2013.01); *F04C 2240/30* (2013.01)

(58) Field of Classification Search
CPC .... F04C 2/084; F04C 2/08; F04C 2/18; F04C 13/00
See application file for complete search history.

(56) References Cited

U.S. PATENT DOCUMENTS

| | | |
|---|---|---|
| 3,173,374 A | 3/1965 | Beimfohr |
| 3,986,797 A | 10/1976 | Kopf |

(Continued)

FOREIGN PATENT DOCUMENTS

| | | |
|---|---|---|
| DE | 69105695 | 4/1995 |
| EP | 2140142 | 8/2010 |

*Primary Examiner* — Deming Wan
(74) *Attorney, Agent, or Firm* — Jacobson Holman PLLC

(57) ABSTRACT

The present invention relates to a gear pump having a housing that has an inflow for the liquid to be conveyed, that has an outflow for the conveyed liquid, and that has a pump chamber in which the gear or gears for conveying the liquid are present, with at least one bearing position being present in the housing, in which bearing position at least one gear is rotatably received, wherein the inflow is in a different plane than the outflow; and wherein at least one first flushing passage that extends up to the bearing position(s) is in direct or indirect fluid communication with the inflow and/or with the outflow.

12 Claims, 3 Drawing Sheets

Figure 1:
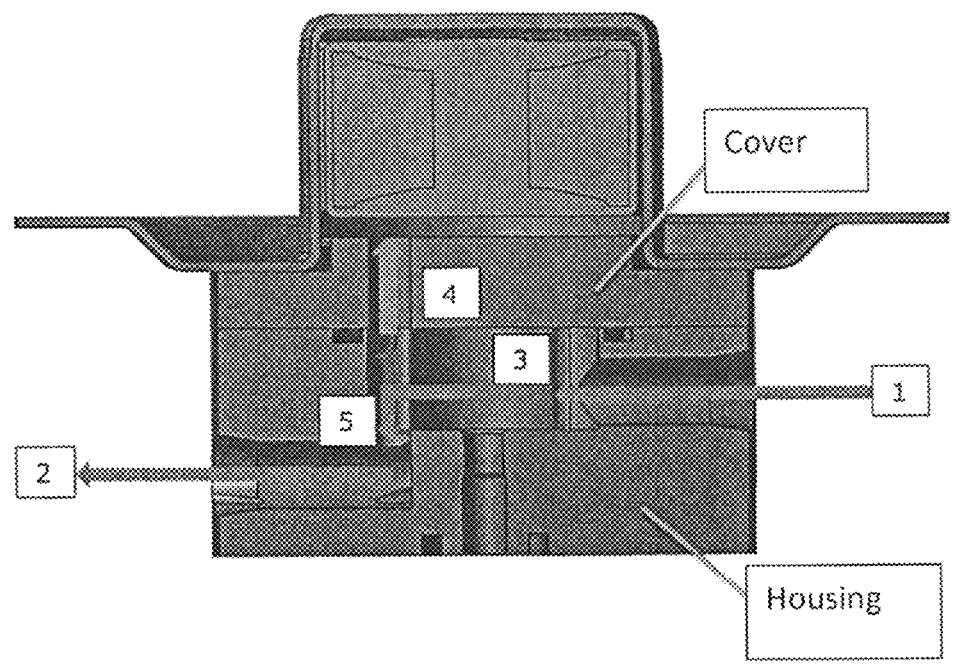

(51) Int. Cl.
*F04C 13/00* (2006.01)
*F04C 2/18* (2006.01)
*A61M 60/113* (2021.01)
*A61M 60/845* (2021.01)
*A61M 60/457* (2021.01)
*A61M 60/37* (2021.01)
*A61M 60/253* (2021.01)
*F04C 14/26* (2006.01)
*F04C 15/06* (2006.01)

(56) References Cited

U.S. PATENT DOCUMENTS

| | | |
|---|---|---|
| 6,206,666 B1 | 3/2001 | Steinrock et al. |
| 6,692,244 B2 * | 2/2004 | Bhagavatula ....... F04C 15/0046 418/206.7 |
| 2005/0042124 A1 | 2/2005 | Miyagi |
| 2014/0145684 A1 | 5/2014 | Liu et al. |
| 2015/0132172 A1 * | 5/2015 | Reimann ............... F01C 21/108 418/205 |
| 2018/0118049 A1 | 5/2018 | Ko |
| 2018/0372806 A1 | 12/2018 | Laughery et al. |

* cited by examiner

GEAR PUMP

The present invention relates to a gear pump comprising a housing that has an inflow for liquid to be conveyed and an outflow for the conveyed liquid and that has a pump chamber in which the gear or gears for conveying the liquid is/are located, wherein a bearing position is present in the housing, in which bearing point the gear or gears or their axle/axles is/are received.

Gear pumps are displacement pumps in which the liquid is conveyed from the suction side to the pressure side by the movement of the gears. Gear pumps typically have two gears that engage into one another; however, pumps are also covered by the invention that only have one gear and in which the displacement of the liquid takes place between the gear and a housing part in which the gear is rotatably received.

The gear or gears or their axle or axles is/are typically rotatably received in sliding bearings in known gear pumps, with the sliding bearings being provided with a lubricant to ensure low-friction and low-noise operation. This is, however, associated with the disadvantage that lubricant can also enter into the liquid to be conveyed, which is in particular not desirable in medical applications.

It is therefore the underlying object of the present invention to further develop a gear pump of the initially named kind such that the risk of contamination of the liquid to be conveyed with lubricant is reduced.

This object is achieved by a first gear pump having a housing that has an inflow for the liquid to be conveyed, that has an outflow for the conveyed liquid, and that has a pump chamber in which gear or gears for conveying the liquid are present, with at least one bearing position being present in the housing, and in which bearing position at least one gear is rotatably received, characterized in that the inflow is in a different plane than the outflow; and in that at least one first flushing passage that extends up to the bearing position(s) is in direct or indirect fluid communication with the inflow and/or with the outflow. The object is also achieved by a second gear pump having a housing that has an inflow for the liquid to be conveyed, that has an outflow for the conveyed liquid, and that has a pump chamber in which gear or gears for conveying the liquid are present, with at least one bearing position being present in the housing, and in which bearing position at least one of the gears is rotatably received, and with a magnet for driving the gear or gears being located in the housing, characterized in that a second flushing passage that extends up to the magnet is located on the pressure side of the gears.

Provision is accordingly made that the inflow is located in a different plane than the outflow and that a first flushing passage that extends up to the bearing position is in direct or indirect fluid communication with the inflow and/or with the outflow. The bearing position is thus independently flowed around by the liquid to be conveyed or by the conveyed liquid (called the "conveying liquid" in the following) that thus simultaneously serves as a lubricant. A dry running of the bearing position(s) is thus effectively prevented even without the use of a separate lubricant.

The first flushing passage extends from the inflow or from the outflow or from one of passages in fluid communication with them and opens into the bearing position(s) for the gears, with the level difference between the inflow and the outflow providing the opportunity for the creation of a downcomer that is always flowed through when the pump is in operation. The first flushing passage preferably branches off from the downcomer. The downcomer preferably likewise extends from the pressure side of the pump to the outflow.

Provision is made in a further variant that a magnet for driving the gears is present in or at the housing and that a second flushing passage is located at the pressure side of the gears that extends up to the magnet. This second flushing passage is likewise flowed through when the pump is in operation, with the conveying liquid moving up to and into the rotating region of the magnet so that it is flowed around by the medium and no dry running arises in the region of the coupling to the gear or gears. A separate lubricant is thus also not required here.

A combination of the two aforesaid ideas is also conceivable so that the first gear pump can be configured with the features of the second gear pump.

The inflow is preferably arranged higher than the outflow and a downcomer is provided that extends over the level difference or over a part thereof between the inflow and the outflow, with the downcomer being in fluid communication with the flow passage or passages.

The bearing position(s) for the axles of the gears is/are preferably sliding bearings.

The housing of the gear pump can be made up of a plurality of individual layers, for example of metal plates or the like. Two or three separate layers can be provided that are connected to one another, which enables an easy production and an easy dismantling with few possibilities of contamination.

It is conceivable that one layer forms the base housing body and one layer forms a cover or a cover layer, with the inflow, the pump chamber, and the outflow being arranged in the base housing body, and with the magnet for driving the gear or gears being arranged in the cover layer.

The pump chamber can be located at the level of the inflow and the outflow can be located below this level.

The first and second flushing passages are preferably in fluid communication with one another so that the conveying liquid flows around both the bearing(s) for the gears and the region between the magnet and the gear(s) in operation of the pump.

The present invention further relates to the use of a gear pump in accordance with the invention for conveying biological or medical fluids, in particular for conveying fluid used for preparing a dialysis solution such as water, or for conveying a ready-to-use dialysis solution.

The present invention furthermore relates to the use of a gear pump in accordance with the invention in a blood treatment device, in particular in a dialysis machine. The gear pump preferably serves as a degassing pump.

The present invention further relates to a blood treatment device, in particular a dialysis machine, having a gear pump in accordance with the invention.

The above statements with respect to the position of the elements of the pump such as the inlet, outlet, pump chamber, etc. relate to the pump in the state of use. This is preferably the state in which the pump is vertical, with in this state, the inflow and the outflow extending horizontally, and with the gears also being in a horizontal plane. The first flushing passage preferably extends laterally, such as horizontally, and the second flushing passage extends upwardly, preferably vertically. The magnet is preferably above the gear or gears.

It is pointed out here that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment shown in the drawing.

Figure 2:
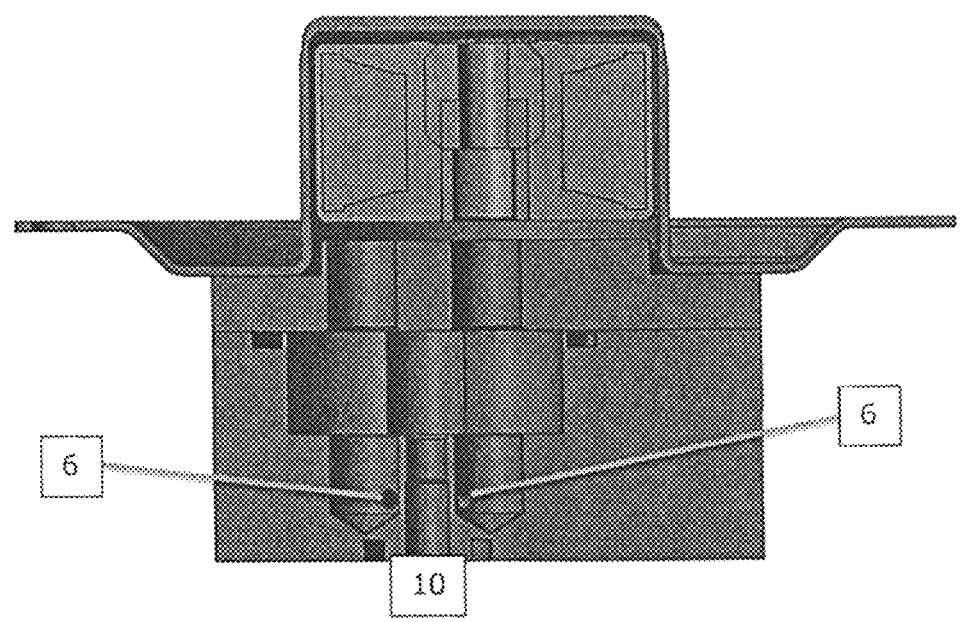
Figure 3:
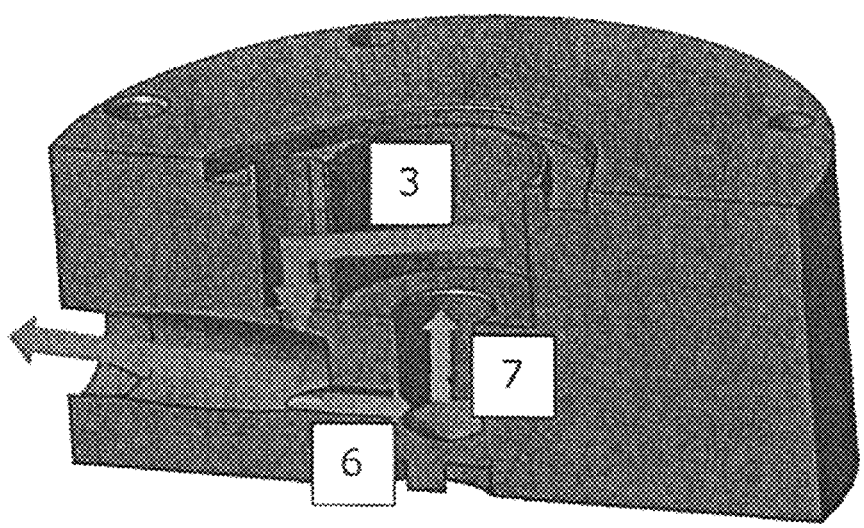
Figure 4:
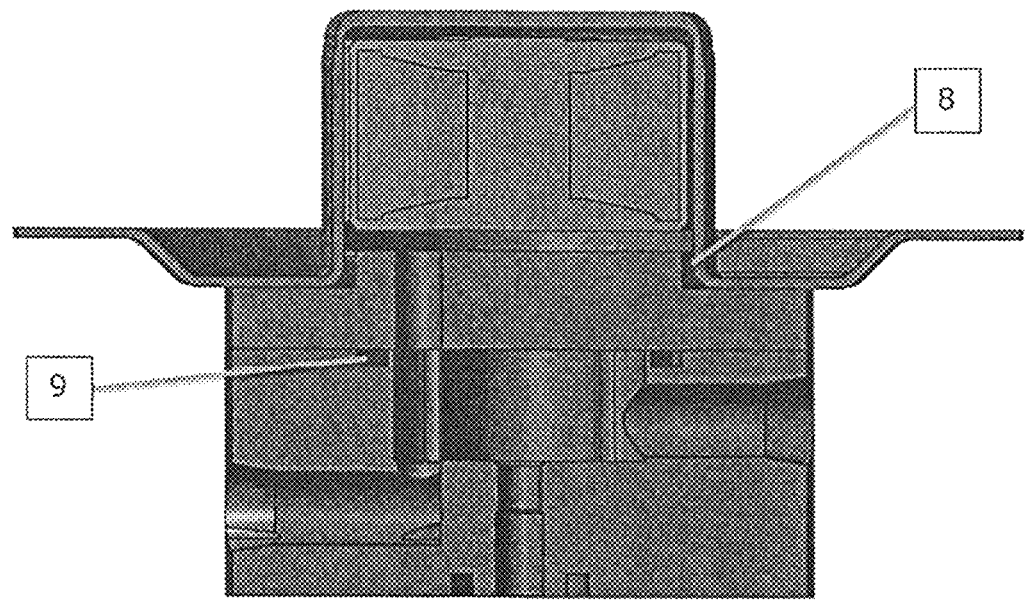

There are shown:

FIG. 1: a sectional view through the gear pump;

FIG. 2: a further sectional view of the gear pump with first flushing passages;

FIG. 3: a sectional view through the base housing body;

FIG. 4: a further sectional view of the gear pump with sealing regions; and

Figure 5:
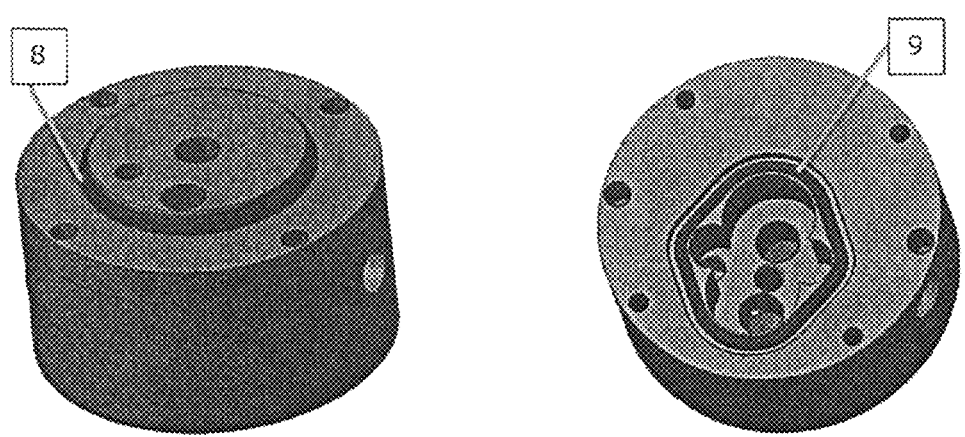

FIG. 5: perspective views of the housing and of the base housing body.

FIG. 1 shows a gear pump in accordance with the invention having the base housing body G and having the cover layer D that is placed onto the base housing body G in a fluid-tight manner.

The inlet or inflow 1 for the medium to be conveyed is located in the base housing body G and leads to the pump chamber 3 in which the gears, not shown, are located. The passage 5 that is arranged vertically and that opens into the outlet or outflow 2 is located at the pressure side of the pump chamber 3, i.e. to the left thereof in accordance with FIG. 1.

The second flushing passage 4 that leads to the magnet M located above the cover layer D is located in the cover layer D. The magnet cooperates with at least one of the gears such that a rotational movement of the magnet produces a rotational movement of the gear or gears.

Liquid is conveyed through the housing into the pump chamber 3 through the inlet 1. It is distributed by the rotation of the gear or gears in the pump chamber 3 and moves via the second flushing passage or supply passage 4 in the cover D into the rotational region of the magnet M so that the latter is flowed around by liquid and no dry running arises in the region of the coupling to the gear. The passages 4 and 5 are disposed exactly above one another so that optimum flow and stream conditions are ensured.

Some of the conveying liquid thus moves from the passage into the outflow 2 and some moves via the second flushing passage 4 into the region of the magnet M.

FIG. 2 shows a view of the pump in which the first flushing passages 6 are visible whose arrangement can be seen better from FIG. 3.

The conveying fluid moves automatically via the downcomer 5 to the outlet due to the vertical offset between the inflow 1 and the outflow 2, said outlet being disposed at a lower level than the inlet and than the pump chamber 3, without a movement of the gear or gears being required for this purpose. The downcomer 5 serves as a supply passage for the first flushing passage 6 that can, like all the other passages, be designed as a bore.

The first flushing passage 6 is thus in fluid communication with the sliding bearing position 7 and supplies it with conveying liquid from below. The liquid moves from there into the pump chamber 3 and then back into the downcomer 5 again so that a circuit flow is produced.

It is thereby ensured that the sliding bearing position 7 is always supplied with liquid and no separate lubricant is required. This has a positive effect on the sliding bearing position(s) 7.

The pump in accordance with the invention preferably does not have any lubricant (except for the conveying liquid).

The rotational movement of the shaft of the gear or gears in the sliding bearing bore 7 and the inflow of constantly fresh liquid through the first flushing line 6 supply the bearing position 7 with constantly fresh medium which is simultaneously the lubricant for the bearing position 7 and which renews itself by this effect.

The conveying liquid is constantly in motion in all the regions of the pump relevant to function due to the continuous flow. The relevant regions are thus constantly flowed around and no germ formation occurs due to dead branches or other dead zones not present.

FIG. 5 shows the arrangement of a sealing ring 8 and of a seal 9 on the base housing body G (right hand representation) or on the cover D (left hand representation), with the seal 9 sealing between the base housing body G and the cover D, and with the seal 8 sealing between the cover D and a cover A of the gear pump, i.e. toward the outside.

The position of the seals 8, 9 is designed such that the production of dead zones is precluded. Gap formation between the cover D and the base housing body G is likewise precluded by the very tight positioning of the seal 9 that runs around the pump chamber 3. The very small surface is constantly flushed by the movement of the liquid; no germ formation thus occurs.

Providing a bypass passage 10 (cf. FIG. 2) that serves the pressure regulation of the pump is conceivable. This bypass passage extends from the inflow through the first two flushing lines 6 to the outflow 2. The pressure regulation takes place via a bypass screw that is inserted into the bypass bore 10. Its sealing takes place via the geometry at the bypass screw so that the use of an O ring is not required.

The invention claimed is:

1. A gear pump having a housing that has an inflow for the liquid to be conveyed, that has an outflow for the conveyed liquid, and that has a pump chamber in which gear or gears for conveying the liquid are present, with at least one bearing position being present in the housing, in which bearing position at least one of the gears are rotatably received, characterized in that the outflow is in a plane and the inflow is in a different plane than the outflow; and in that at least one first flushing passage that extends up to the bearing position(s) is in direct or indirect fluid communication with the inflow and/or with the outflow, and characterized in that, in a state in which the pump is vertical and in which the inflow and the outflow extend horizontally, the pump chamber is located at the level of the inflow and the outflow is located below the level of the inflow.

2. A gear pump in accordance with claim 1 further comprising a magnet for driving the gear or gears being located in the housing and a second flushing passage that extends up to the magnet and is located on the pressure side of the gears.

3. A gear pump in accordance with claim 2, characterized in that the first and second flushing passages are in fluid communication with one another.

4. A gear pump in accordance with claim 1, characterized in that the inflow is arranged higher than the outflow; and in that a downcomer is provided that extends over the level difference or over a part thereof between the inflow and the outflow, with the downcomer being in fluid communication with the first flushing passage or passages.

5. A gear pump in accordance with claim 1, characterized in that the bearing position is a sliding bearing.

6. Use of a gear pump in accordance with claim 1 for conveying biological or medical fluids, in particular for conveying liquid to prepare a dialysis solution or for conveying a dialysis solution.

7. Use in accordance with claim 6, characterized in that the gear pump serves as a degassing pump.

8. Use of a gear pump in accordance with claim 1 in a blood treatment device, in particular in a dialysis machine.

9. A blood treatment device, in particular a dialysis machine, having a gear pump in accordance with claim 1.

10. A gear pump having a housing that has an inflow for the liquid to be conveyed, that has an outflow for the conveyed liquid, and that has a pump chamber in which gear or gears for conveying the liquid are present, with at least one bearing position being present in the housing, in which bearing position at least one of the gears is rotatably received, and with a magnet for driving the gear or gears being located in the housing, characterized in that a flushing passage that extends up to the magnet is located on the pressure side of the gears, and characterized in that, in a state in which the pump is vertical and in which the inflow and the outflow extend horizontally, the pump chamber is located at the level of the inflow and the outflow is located below the level of the inflow.

11. A gear pump in accordance with claim 10, characterized in that the housing is made up of a plurality of individual layers.

12. A gear pump in accordance with claim 11, characterized in that one of the layers forms a base housing body and one of the layers forms a cover or a cover layer, with the inflow, the pump chamber, and the outflow being arranged in the base housing body, and with the magnet for driving the gear or gears being arranged in the cover layer.

\* \* \* \* \*